US008527034B2

(12) United States Patent
Schroder et al.

(10) Patent No.: US 8,527,034 B2
(45) Date of Patent: Sep. 3, 2013

(54) IMAGE DERIVED INPUT FUNCTION FOR PET LUNG ASSESSMENT

(75) Inventors: Tobias Schroder, Somerville, MA (US); Marcos F. Vidal Melo, Newton, MA (US); Guido Musch, Somerville, MA (US); Robert Scott Harris, Wayland, MA (US); Jose G. Venegas, Swampscott, MA (US); Tilo Winkler, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 1396 days.

(21) Appl. No.: 11/775,915

(22) Filed: Jul. 11, 2007

(65) Prior Publication Data

US 2009/0018438 A1    Jan. 15, 2009

(51) Int. Cl.
*A61B 6/00*    (2006.01)
(52) U.S. Cl.
USPC ............................ 600/431; 600/407; 382/128
(58) Field of Classification Search
USPC .................................. 600/407, 431; 382/128
See application file for complete search history.

(56) References Cited

U.S. PATENT DOCUMENTS 5,865,757 A * 2/1999 Hoeft ............................ 600/504
5,961,457 A * 10/1999 Raylman et al. .............. 600/436
2002/0068864 A1 * 6/2002 Bishop et al. ................. 600/407
2004/0236216 A1 * 11/2004 Manjeshwar et al. ........ 600/436
2006/0279724 A1 * 12/2006 Convert et al. ................ 356/39

FOREIGN PATENT DOCUMENTS

WO    WO 2005/116647 A2    12/2005

OTHER PUBLICATIONS

Tobias Schroder, Marcos F. Vidal Melo, Guidq Musch, R. Scott Harris, Tilo Winkler, and Jose G. Venegas, PET Imaging of Regional 18F-FDG Uptake and Lung Function After Cigarette Smoke inhalation; Massachusetts General Hospital and Harvard Medical School, Boston, MA, J Nucl Med 2007; 48:413-419; Copyright 2007 by Society of Nuclear Medicine, Inc.

* cited by examiner

*Primary Examiner* — Tse Chen
*Assistant Examiner* — Vani Gupta
(74) *Attorney, Agent, or Firm* — Quarles & Brady, LLP

(57) ABSTRACT

An input function indicative of a time-activity curve in pulmonary arterial plasma is produced from a series of PET image frames in lieu of manual blood sampling. Two manually acquired blood samples are input along with pixel values of a blood pool region of interest (ROI) in the PET image frames into a two-parameter model of the ROI's time-activity curve. In an iterative process the model converges to accurately indicate the amount of $^{18}$F-FDG tracer in the arterial blood. Pulmonary uptake of the tracer is assessed with the PET image frames and the calculated input function.

5 Claims, 6 Drawing Sheets

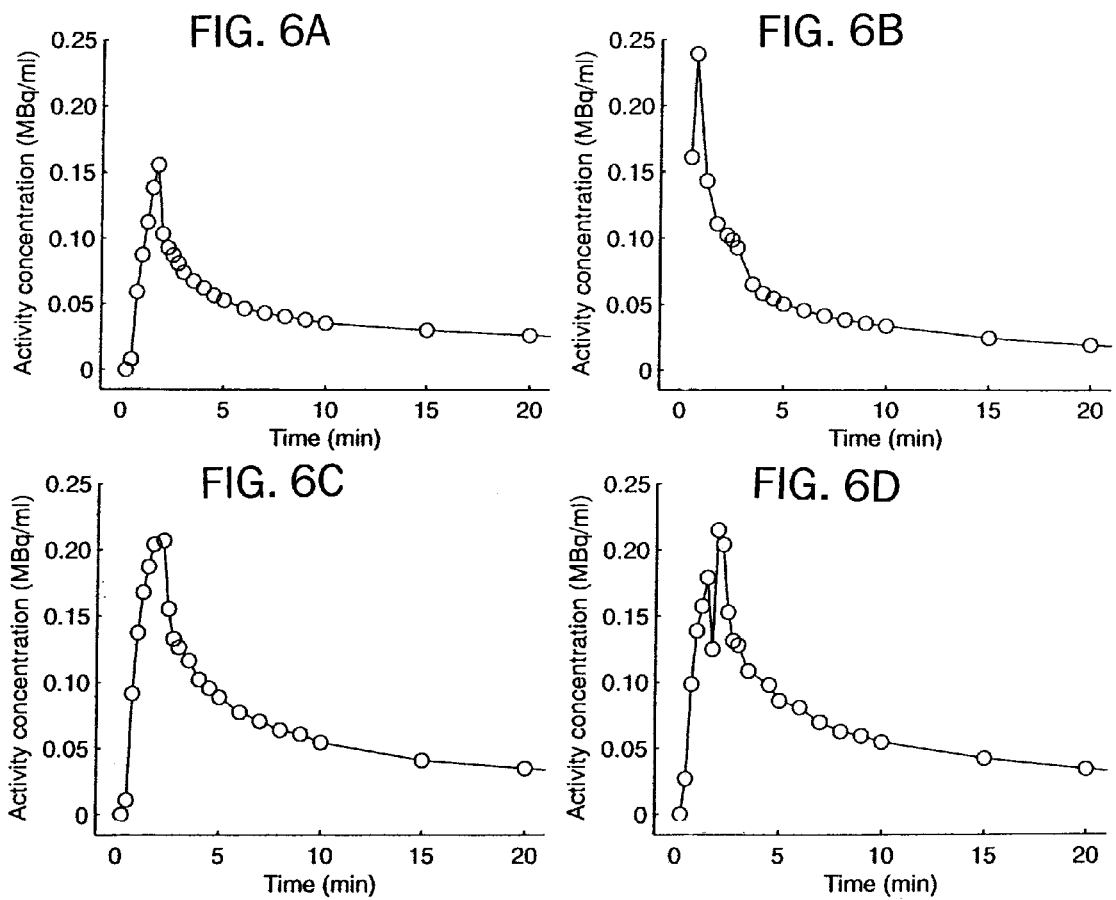

US 8,527,034 B2

IMAGE DERIVED INPUT FUNCTION FOR PET LUNG ASSESSMENT

STATEMENT REGARDING FEDERALLY SPONSORED RESEARCH

This invention was made with government support under Grant Nos. HL086827, HL056879 and HL076464 awarded by the National Institute of Health. The United States Government has certain rights in this invention.

BACKGROUND OF THE INVENTION

The field of the invention is positron emission tomography (PET) scanners, and particularly the quantification of tissue metabolic activity.

Positrons are positively charged electrons which are emitted by radionuclides that have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as blood flow, fatty acid and glucose metabolism, and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners—each gamma ray has an energy of 511 keV and the two gamma rays are directed in nearly opposite directions. An image is created by determining the number of such annihilation events at each location within the scanner's field of view.

Positron-emission tomography (PET) imaging of 2-deoxy-2-[$^{18}$F]fluoro-D-glucose ($^{18}$F-FDG) is increasingly used to assess metabolic activity of pulmonary inflammatory cells. The uptake rate of $^{18}$F-FDG by tissue can be computed either by compartmental modeling or by a graphical technique. A prerequisite for either analysis is the knowledge of the input function to the system in the form of a plasma time-activity curve. Acquisition of such an input function typically involves sequential blood sampling, a process that is invasive, is prone to measurement artifacts, involves radiation and blood exposure to clinical staff, and adds costly laboratory procedures.

To avoid, or minimize, manual blood sampling, substantial effort has been devoted to developing alternative techniques that have been successfully applied to estimate $^{18}$F-FDG uptake in tumors and brain. Some of these known techniques involve population-based assumptions about the input function morphology, while others directly estimate the input function from blood pool regions of interest (ROI) in the PET images.

Analysis of $^{18}$F-FDG uptake by inflamed non-neoplastic lung presents particular challenges which render prior methods unsatisfactory. Population-based assumptions required by prior methods are not available and may vary for different types of pulmonary inflammation. Also, estimates of the input function from blood pool ROI's are affected by partial volume effects, and by activity spillover from the heart or inflamed pulmonary tissues. Moreover, in contrast to brain, heart or solid tumor tissues, where the blood-to-tissue fraction is low, in lung parenchyma blood volume may account for as much as half of the parenchymal volume. As a result, the blood compartment is a dominant source of lung $^{18}$F-FDG activity, and particularly during the early phase following tracer injection. Because early phase kinetics affects estimates of distribution volumes and rapid rate constants, accurate assessment of the early phase input function might be crucial for characterizing the inflamed lung. Although techniques to reduce blood sampling are available, they seem to have limited accuracy in describing the early phase input function, or are unable to assess the early phase of the input function. Current techniques involving image-derived assessment of the early input function either neglect partial volume effects and activity spillover artifacts, or they mathematically correct for these artifacts using measured or approximated anatomic dimensions of the blood pool ROI used.

SUMMARY OF THE INVENTION

The present invention is a method based on a two-parameter model of the input function which separates the ROI's time-activity curve into a blood and an activity spillover compartment. These two parameters are derived using an iterative calculation and two blood samples that are used to calibrate raw PET-derived activity data acquired from a selected ROI in a PET image.

A general object of the invention is to provide an accurate and quantitative input function without the need for taking numerous blood samples. Only two blood samples are acquired when using the present invention and an accurate input function is produced from the event counts that accumulate over time in a selected image ROI. No population-based input function morphology is required and the geometric boundary of the selected blood pool ROI need not be precisely known.

BRIEF DESCRIPTION OF THE DRAWINGS

FIGS. 6A-6D are graphic illustrations of exemplary input functions.

GENERAL DESCRIPTION OF THE INVENTION

Figure 1:
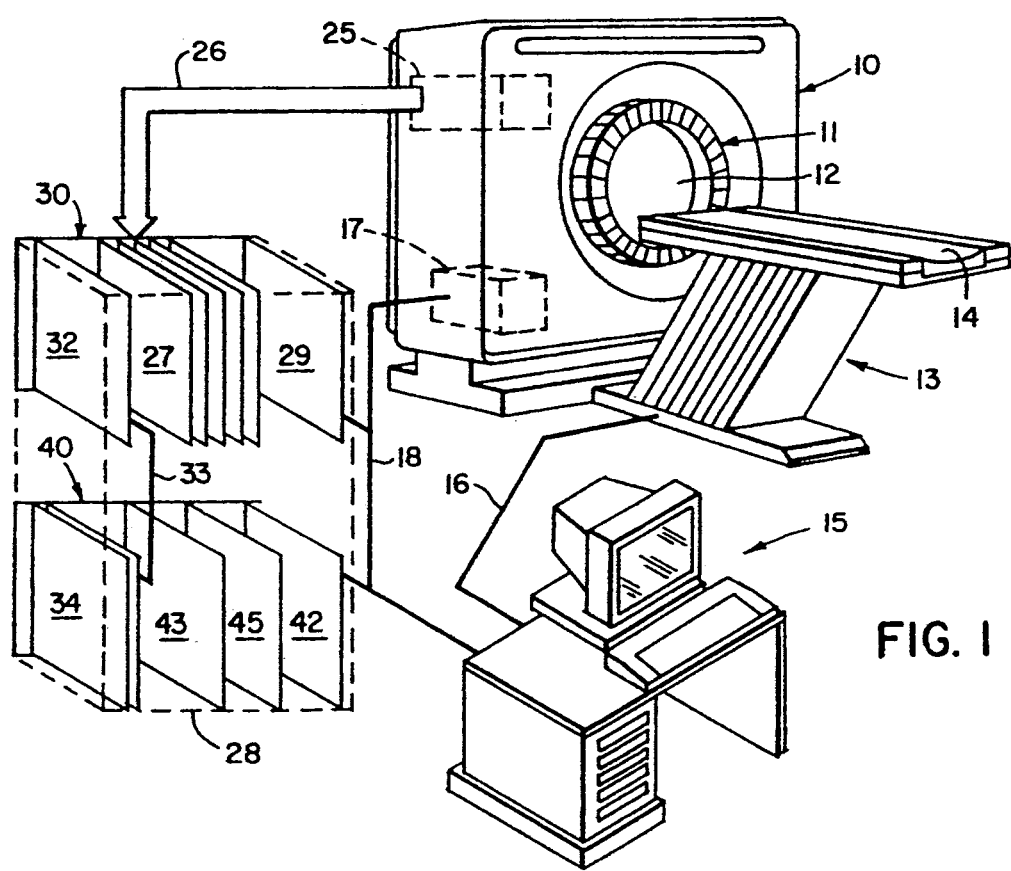
FIG. 1 is a pictorial view with parts cut away of a PET scanner system which employs the present invention.

The PET signal from a blood pool ROI ($C_{PET}(t)$) is modeled by two compartments. One accounts for $^{18}$F-FDG activity from blood plasma ($C_p(t)$), and the other for spillover activity from tracer that accumulates in tissue surrounding the region of interest (ROI). "RC" is defined as a constant recovery coefficient quantifying a geometrical partial volume effect, and "SC" as a constant spillover coefficient from tracer accumulating in the surrounding tissue. The PET signal $C_{PET}(t)$ is expressed as:

$$C_{PET}(t) = RC\,Cp(t) + SC \int_{\tau=0}^{t} Cp(\tau)d\tau \qquad (1)$$

where the integral describes the tracer accumulation in surrounding tissue as a function of $^{18}$F-FDG availability in blood. Dividing both sides of equation (1) by $C_p(t)$ yields:

$$\frac{C_{PET}(t)}{C_p(t)} = RC + \frac{SC \int_{\tau=0}^{t} C_p(\tau) d\tau}{C_p(t)} \quad (2)$$

Assuming that RC and SC are constant during the imaging period, equation (2) becomes a linear equation according to $$y = SCx + RC \quad (3)$$

with the variables $$y = C_{PET}(t)/C_p(t) \quad (4)$$

and $$x = \int_{t=0}^{t} C_p(\tau) d\tau / C_p(t) \quad (5)$$

Figure 3:
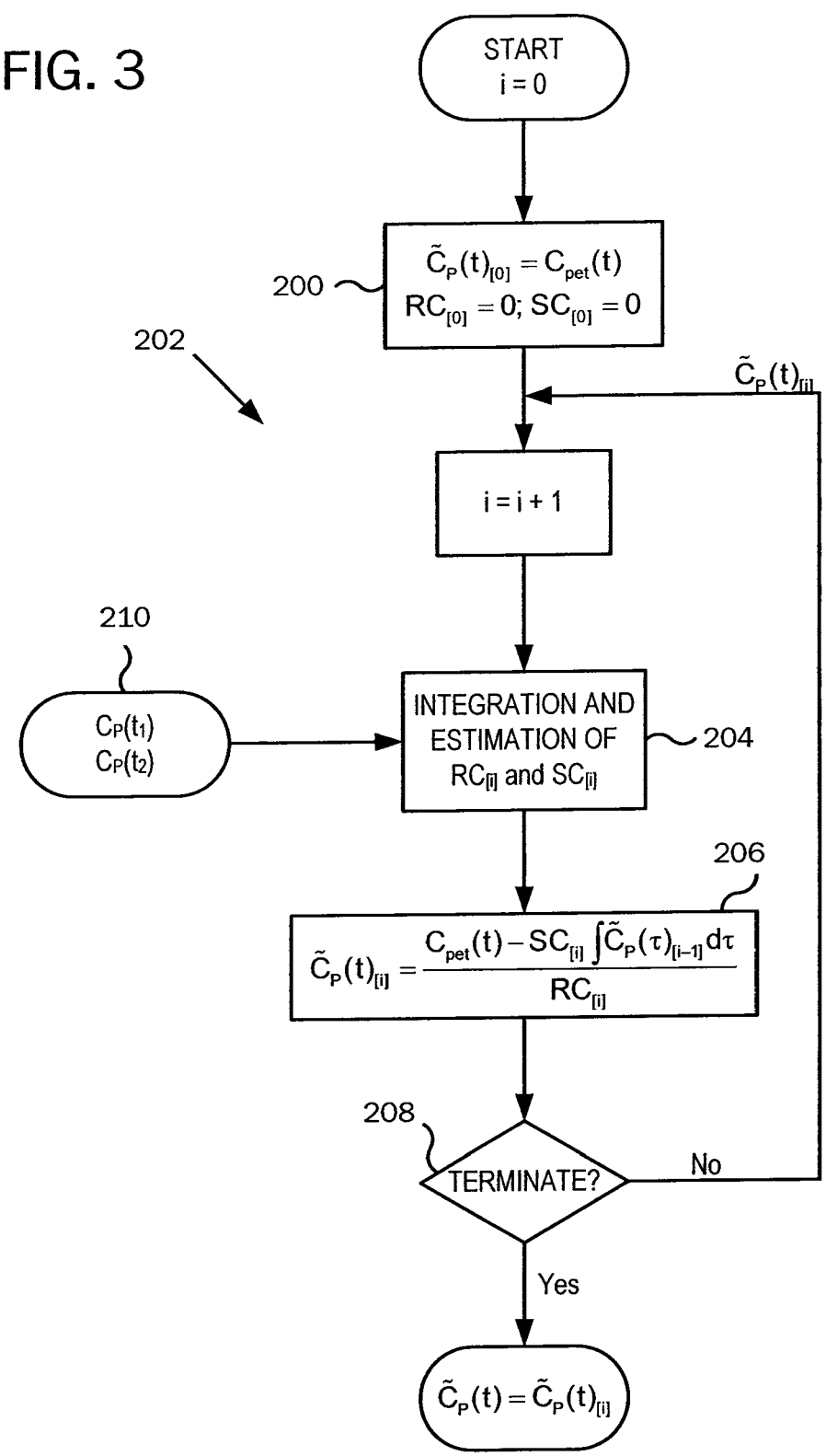
FIG. 3 is a flow chart of the steps used to calculate an input function according to the present invention.

To compute RC and SC by linear regression of equation (3), the integral of the unknown time course of $C_p(t)$ is needed. To solve this dilemma, an iterative process is used, which requires a minimum of two blood sample data points to obtain estimates of RC and SC, and thus, to obtain a model-adjusted, image-derived estimate of $C_p(t)$. As shown in FIG. 3, the iterative process indicated generally at 202 is entered after initialization as indicated at process block 200. For the first iteration, $C_{PET}(t)$ serves as an initial estimate of $C_p(t)$ ($\tilde{C}_p(t)_{[0]}$). Then, the following three steps are iterated. First, the index i is incremented and an approximation of the integral in equation (2) is calculated by the integral of the (i−1)$^{th}$ estimate of $C_p(t)$ ($\tilde{C}_p(t)_{[i-1]}$) as indicated at process block 206.

Two blood samples, obtained at times $t_1$ and $t_2$ ($C_p(t_1)$ and $C_p(t_2)$), are used to compute the current (i$^{th}$) estimates of RC and SC ($RC_{[i]}$ and $SC_{[i]}$) by linear regression as indicated at process block 204. As indicated at process block 206, the new estimate of $C_p(t)$, $\tilde{C}_p(t)_{[i]}$ is calculated:

$$\tilde{C}_p(t)_{[i]} = \frac{C_{PET}(t) - SC_{[i]} \int \tilde{C}_p(t)_{[i-1]} dt}{RC_{[i]}} \quad (6)$$

These three steps are repeated until estimates of plasma activity at $t_1$ and $t_2$ converge to the measured sample values as determined at decision block 208.

Using this model-adjusted input function that, requires only two calibration blood samples as indicated at input 210, unbiased estimates of $^{18}$F-FDG uptake in the normal and inflamed lung are calculated. The method is insensitive to the collection time of the first calibration blood sample $C_p(t_1)$ that can be chosen between 3.5 minutes to 25 minutes after the start of tracer injection. The second calibration sample $C_p(t_2)$ is taken at 50 minutes after injection. More important, the approach performs well with blood pool ROI's affected by activity spillover and/or partial volume, without requiring *a priori* knowledge of a population-based input function morphology or of the exact ROI anatomy.

Detailed Description of the Preferred Embodiment

Referring particularly to FIG. 1, the PET scanner system includes a gantry 10 which supports a detector ring assembly 11 about a central axis, or bore 12. A patient table 13 is positioned in front of the gantry 10 and is aligned with the central axis of the bore 12. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a second serial communication link 18 to operate the gantry 10. For example, the gantry 20 can be tilted away from vertical on command from the operator, it can perform a "transmission scan" with a calibrated radionuclide source to acquire attenuation measurements, or it can perform a normal scan in which positron annihilation events are counted and an image is reconstructed.

Figure 2:
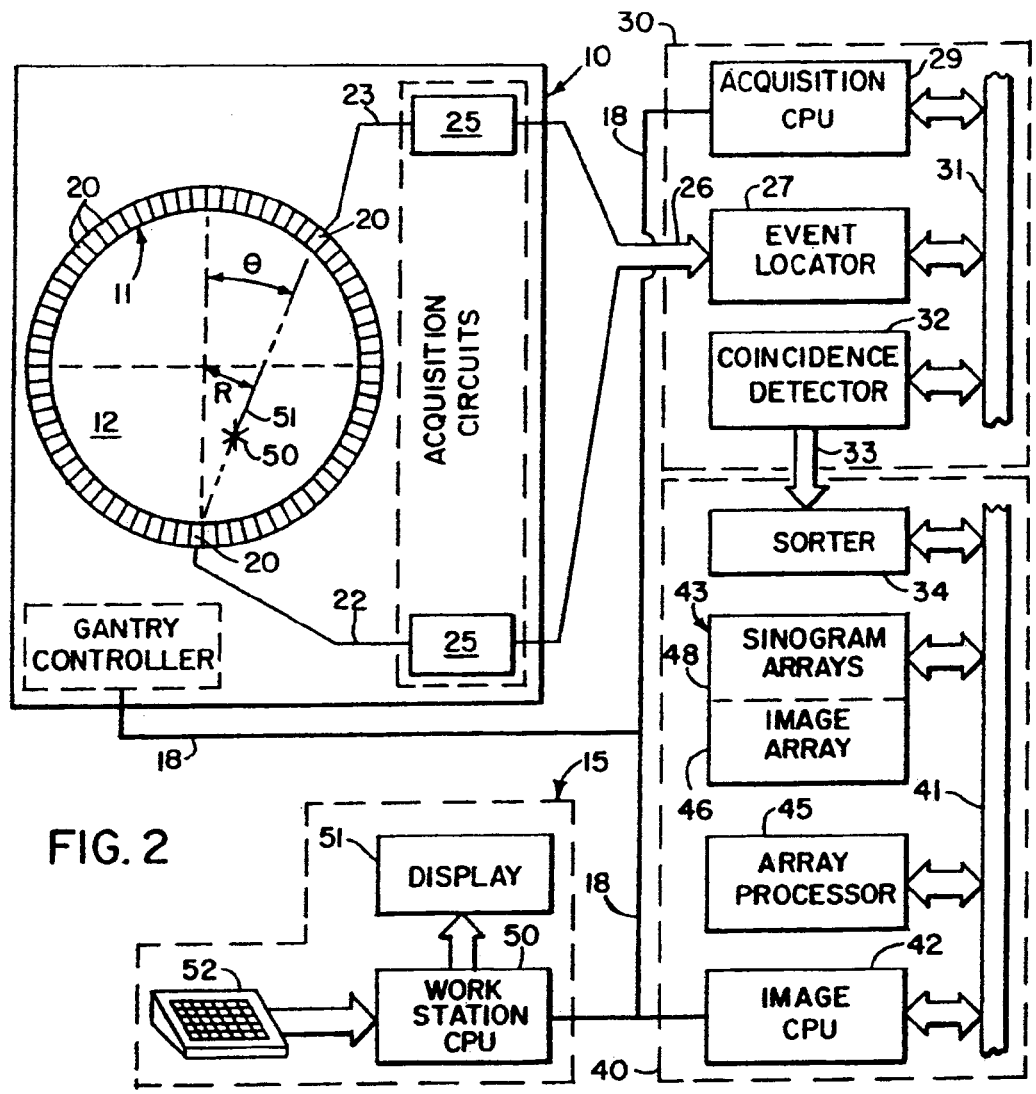
FIG. 2 is a schematic diagram of the PET scanner system of FIG. 1.

Referring to FIGS. 1 and 2, a set of acquisition circuits 25 are mounted within the gantry 10 to receive the signals from detector modules 20 in the detector ring 11. These signals are then digitized and sent through a cable 26 to an event locater circuit 27 housed in a separate cabinet 28. Each acquisition circuit 25 also produces an event detection pulse (EDP) which indicates the exact moment the scintillation event took place.

Referring particularly to FIGS. 1 and 2, the event locator circuits 27 form part of a data acquisition processor 30 which periodically samples the signals produced by the acquisition circuits 25. The processor 30 has a backplane bus structure 31, and an acquisition CPU 29 which controls communications on this bus 31 and links the processor 30 to the local area network 18. The event locator 27 is comprised of a set of separate circuit boards which each connect to the cable 26 and receive signals from the corresponding acquisition circuits in the gantry 10. The event locator 27 synchronizes the event with the operation of the processor 30 by detecting the event pulse (EDP) produced by an acquisition circuit 25, and converting it into an 8-bit time marker which indicates when within the current sample period the scintillation event took place. Also, this circuit 27 discards any detected events if the total energy of the scintillation is outside the range of 511 keV±20%. During each sample period, the information from detector ring 11 is assembled into a set of digital numbers that indicate precisely when an event took place and the position of the detector modules 20 which detected the event. This event data packet is conveyed to a coincidence detector 32 which is also part of the data acquisition processor 30.

The coincidence detector 32 accepts the event data packets from the event locators 27 and determines if any two of them are in coincidence. Coincidence is determined by a number of factors. First, the time markers in each event data packet must be within a preset time window of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a link 33 to a sorter 34. Each coincidence data packet is a data stream which includes a pair of digital numbers that precisely identify the location of the two detector modules 20 that detect the event.

The sorter 34 is a circuit which forms part of an image reconstruction processor 40. The image reconstruction processor 40 is formed about a backplane bus 41. An image CPU 42 controls the backplane bus 41 and it links the processor 40 to the local area network 18. A memory module 43 also connects to the backplane 41 and it stores the data used to reconstruct images. An array processor 45 also connects to the backplane 41 and it operates under the direction of the image CPU 42 to perform the image reconstruction using the data in memory module 43. The resulting image array 43 is stored in a memory module 46 and is output by the image CPU 42 to the operator work station 15.

The function of the sorter 34 is to receive the coincidence data packets and generate from them memory addresses for the efficient storage of the coincidence data. The set of all projection rays that point in the same direction (θ) and pass through the scanner's field of view is a complete projection, or "view". The distance (R) between a particular projection ray and the center of the field of view locates that projection ray within the view. As shown in FIG. 2, for example, an event 50 occurs along a projection ray 51 which is located in a view at the projection angle θ and the distance R. The sorter 34 counts all of the events that occur on this projection ray (R, θ) during the scan by sorting out the coincidence data packets that indicate an event at the two detectors lying on this projection ray. The coincidence counts are organized in memory 43 as a set of two-dimensional arrays, one for each axial image plane, and each having as one of its dimensions the projection angle θ and the other dimension the distance R. This θ by R map of the measured events is called a histogram, or more commonly a sinogram array 48.

Figure 4:
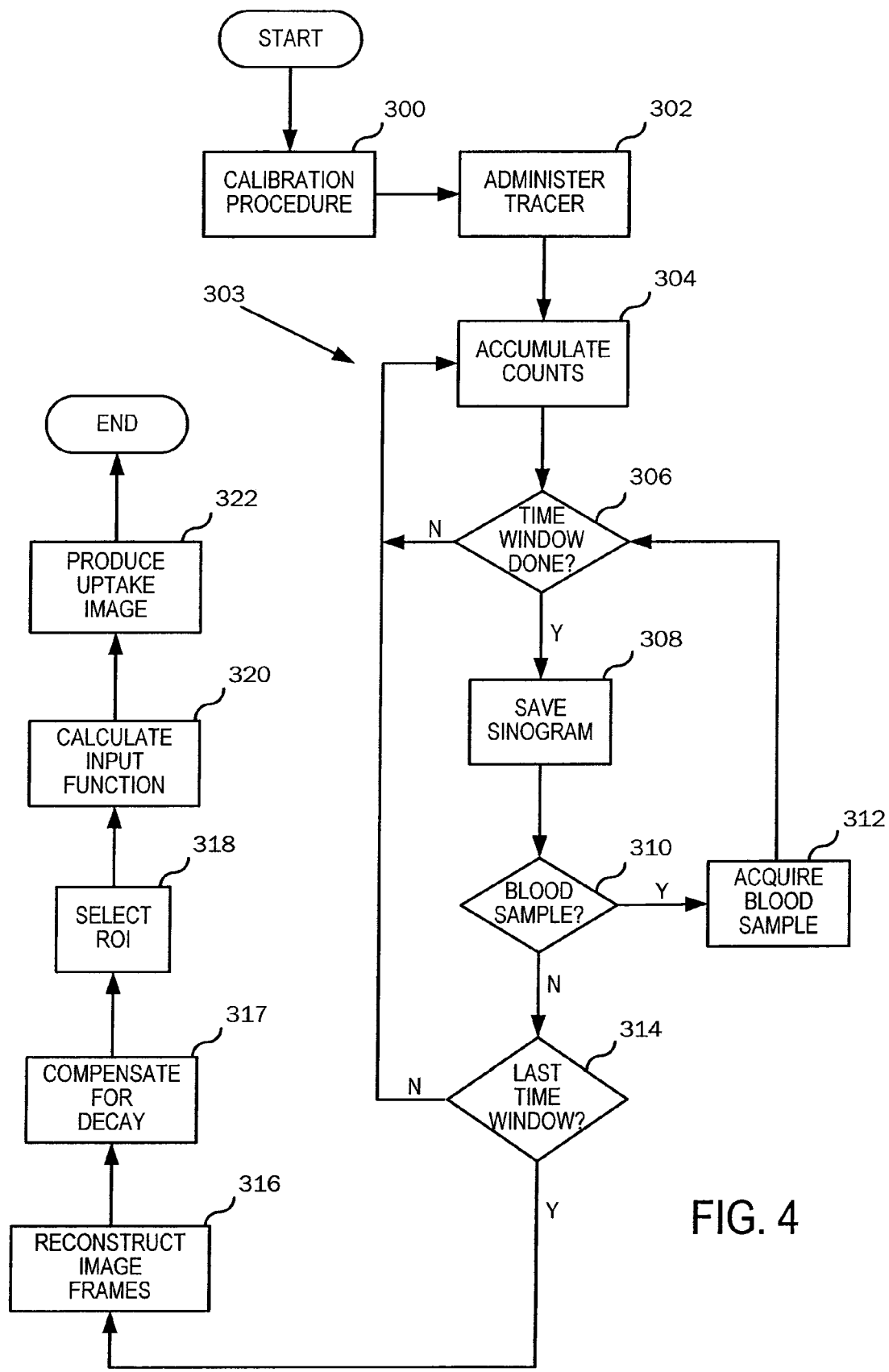
FIG. 4 is a flow chart of a preferred PET scan which employs the input function produced in FIG. 3.

Referring particularly to FIG. 4, the present invention is employed in a procedure which measures the uptake of the tracer $^{18}$F-FDG in the lungs of a subject placed in the bore of the PET system. The first step is to calibrate the system as indicated at process block 300 using well known PET attenuation correction methods. The $^{18}$F-FDG tracer is then administered to the subject as indicated at process block 302, and a loop indicated generally at 303 is entered in which positron annihilation events are counted over a series of time windows. For its administration, about 370 MBq of $^{18}$F-FDG tracer is dissolved in 10 ml of saline and injected with a standard injection pump at a constant rate of 10 ml/min into a vein. This is followed by a flush of normal saline at the same rate.

Figure 5:
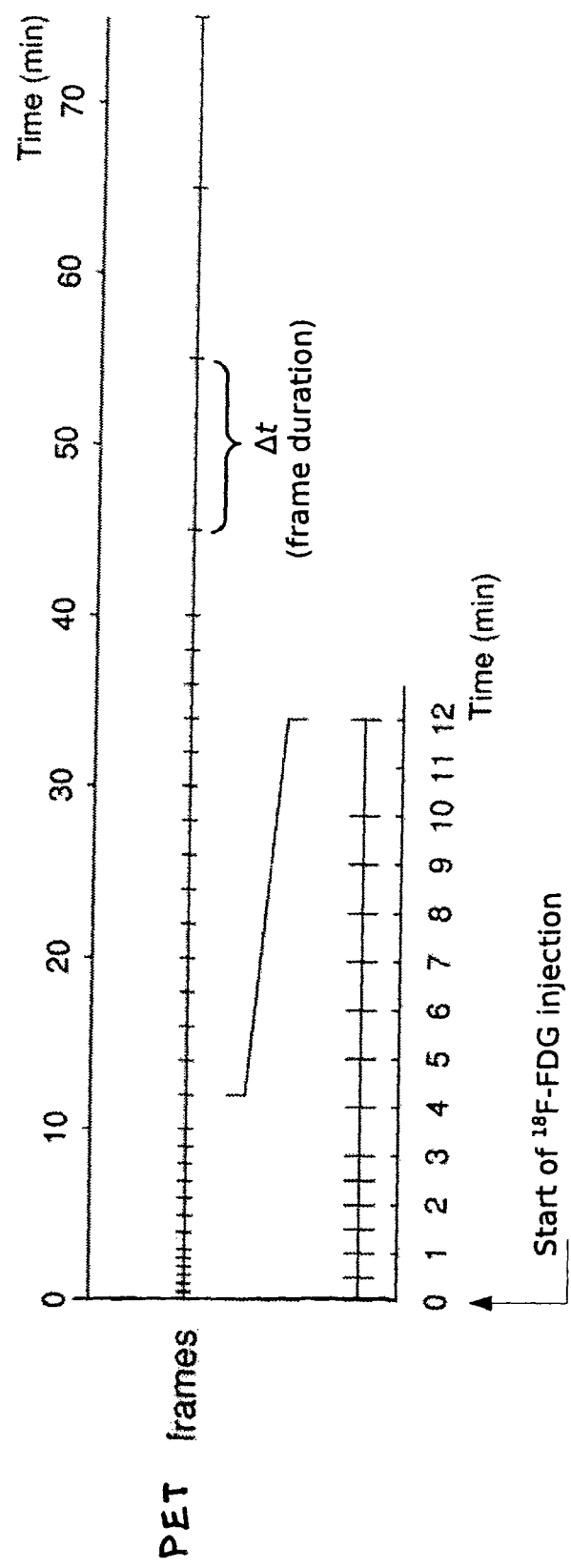
FIG. 5 is a graphic illustration of the variable time windows used during the procedure.

The annihilation events are counted as indicated at process block 304 until the end of a time window is detected at decision block 306. As described above, the counts accumulate to form a sinogram array 48 and at the end of each time window the sinogram is saved as indicated at process block 308. Time windows are kept as short as possible to increase the time resolution of the tracer uptake curve, but they must be long enough to enable sufficient counts to accumulate to reconstruct an image frame of the desired signal-to-noise ratio (SNR). Typically, the time window is set from 30 s to 120 s, but as shown in FIG. 5, it is preferable to vary the time window during the scan such that the time resolution is greater at the start when the input function is changing in magnitude at a higher rate.

In the preferred embodiment the time window for the initial PET image frames is 30 seconds and it is increased to 1 minute, then 2 minutes, then 5 minutes and finally 10 minutes. Although it is possible to maintain the initial high frame rate throughout the scan, the benefits of the uniformly sampled image frames is offset by a decrease in the statistical reliability of the nuclear counting results during the later phases of the scan. This in large part is due to the decline in activity of the radioisotope over time. The system remains in the loop 303 to acquire a series of sinograms over the prescribed time period as determined at decision block 314. This completes the data acquisition phase of the procedure.

Referring still to FIG. 4, during the data acquisition phase two blood samples are acquired as determined at decision block 310. Typically, a first blood sample $C_p(t_1)$ is acquired as indicated at process block 312 from 3.5 to 25 minutes into the data acquisition phase, and the second sample $C_p(t_2)$ is acquired at approximately 50 minutes into the acquisition phase. Each blood sample is acquired by drawing 1 ml of venous blood, which is spun down to obtain the plasma fraction. The activity concentration is measured in a well counter that has been cross calibrated with the PET camera. The measured concentration of the tracer in the sample blood is input to the system for use during the post processing phase described below.

After the acquisition phase is completed a series of image frames are reconstructed from the stored series of acquired sinograms as indicated at process block 316. This is a conventional filtered backprojection image reconstruction and the resulting image frames are interpolated to form a 128×128×15 voxel image array.

As indicated at process block 317, to compensate for the radioactive decay of the tracer, the known half-life of the tracer is used to adjust the activity measurements in each acquired image frame with reference to the starting time of the scan. As indicated at process block 318, the next step is to select an ROI in the image frames which will provide an accurate indication of the tracer concentration in the subject's venous blood. Preferably the ROI is selected to be the blood pool in the right or left heart chambers or the descending aorta. Selection of the boundary of one of these blood pools can be facilitated by producing other images, although it has been discovered that accuracy of the method is very insensitive to the accuracy with which the ROI boundary is defined.

As indicated at process block 320, the next step is to calculate the input function as described in detail above. This employs the ROI image voxels in all of the reconstructed image frames as well as the two acquired blood samples. The process is repeated until the image derived input function corresponds to the measured blood samples at time $t_1$ and $t_2$. The iterative process for calculating the input function has been found to converge to an accurate input function curve in about six iterations.

Exemplary calculated input functions are plotted in FIGS. 6A-6D. The shape of the input function varies substantially among subjects as well as the particulars of the scan procedure. For example, a bolus injection time of 1.5 minutes results in a longer peak phase as shown in FIG. 6C as compared to a 1.0 minute bolus injection time as shown in FIG. 6A. Another variation in the earlier phase of the input function is caused by a delay between the end of a bolus injection of the tracer and the beginning of the saline flush required to remove remaining tracer from the infusion system. Such a time delay can result in discontinuities during the peak phase of the input function as shown in FIG. 6D. FIG. 6B depicts a manually sampled input function afflicted by poor timing of the operator, i.e., tracer administration and manual blood sampling were started non-simultaneously. In this case, the manually sampled input function is not suitable to analyze early-phase tracer kinetics in blood and tissue. Conversely, the disclosed procedure can provide an accurate input function by using two blood samples taken during the later phase of imaging where blood activity changes slowly over time.

And finally, the image frames and the input function are employed to produce an uptake image. For each image voxel the tracer uptake curve for that voxel as revealed in the series of acquired image frames and as determined using the calculated input function. A tracer uptake value for the voxel is calculated as described by T. Schroeder et al "PET Imaging of Regional $^{18}$F-FDG Uptake and Lung Function After Cigarette Smoke Inhalation", *The Journal of Nuclear Medicine*, Vol. 48, No. 3, March 2007. The resulting uptake image thus indicates the metabolic activity of tissues located at each image voxel.

The invention claimed is:

1. A method for calculating an input function for use in the assessment of lung activity in a subject, the steps comprising:
    a) administering a radionuclide tracer to the subject;
    b) acquiring a series of image frames with a positron emission tomographic (PET) system;
    c) acquiring two blood samples from the subject during the performance of step b);
    d) designating a blood pool region of interest (ROI) in the image frames; and
    e) calculating the input function using information in the two blood samples, using values in the image frames corresponding to the designated blood pool ROI, and using a two-parameter model of the ROI time-activity curve.

2. The method as recited in claim 1 in which the blood pool ROI is selected from one of a heart chamber or the aorta in the subject.

3. The method as recited in claim 1 in which the radionuclide tracer is 2-deoxy-2-[18F] fluoro-D-glucose (18F-FDG).

4. The method as recited in claim 1 in which step e) is an iterative process in which the two-parameter model is adjusted until its time-activity curve corresponds with the two blood samples.

5. The method as recited in claim 1 in which the two parameters in said two-parameter model are a recovery coefficient (RC) quantifying a geometrical partial volume effect, and a spillover coefficient (SC) from tracer accumulating in surrounding tissue.

* * * * *